United States Patent
Fujioka et al.

(10) Patent No.: US 10,041,884 B2
(45) Date of Patent: Aug. 7, 2018

(54) NUCLEIC ACID ANALYZER AND NUCLEIC ACID ANALYSIS METHOD USING SAME

(71) Applicant: Hitachi High-Technologies Corporation, Tokyo (JP)

(72) Inventors: Michiru Fujioka, Tokyo (JP); Motohiro Yamazaki, Tokyo (JP); Toru Yokoyama, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 164 days.

(21) Appl. No.: 14/890,246

(22) PCT Filed: May 9, 2014

(86) PCT No.: PCT/JP2014/062494
§ 371 (c)(1),
(2) Date: Nov. 10, 2015

(87) PCT Pub. No.: WO2014/188887
PCT Pub. Date: Nov. 27, 2014

(65) Prior Publication Data
US 2016/0109368 A1   Apr. 21, 2016

(30) Foreign Application Priority Data
May 24, 2013 (JP) .................. 2013-109975

(51) Int. Cl.
*G01N 21/64* (2006.01)
*G06F 19/24* (2011.01)
*C12Q 1/68* (2018.01)

(52) U.S. Cl.
CPC .......... *G01N 21/6486* (2013.01); *C12Q 1/68* (2013.01); *G01N 21/6408* (2013.01);
(Continued)

(58) Field of Classification Search
None
See application file for complete search history.

(56) References Cited

U.S. PATENT DOCUMENTS 6,821,402 B1   11/2004   Sharaf et al.
2002/0125136 A1   9/2002   Sharaf et al.
(Continued)

FOREIGN PATENT DOCUMENTS

| JP | 05-240837 A | 9/1993 |
|---|---|---|
| JP | 2002-525576 A | 8/2002 |

(Continued)

OTHER PUBLICATIONS

International Search Report of PCT/JP2014/062494.
German Office Action received in corresponding German Application No. 11 2014 002 045.1 dated Dec. 7, 2016.

*Primary Examiner* — Shawn Decenzo
(74) *Attorney, Agent, or Firm* — Mattingly & Malur, PC

(57) ABSTRACT

Provided is a nucleic acid analyzer, which does not require manual processes by a highly trained operator such as a researcher and is easy to use, small-sized, capable of accepting multiple samples, and performs speedy analysis, and a nucleic acid analysis method using the analyzer. The analyzer and method perform detection in a plurality of exposure times, provide a program for determining a threshold for signal detection, and determine whether a faint signal peak is a false signal peak.

16 Claims, 11 Drawing Sheets

(52) U.S. Cl.
CPC ..... *G06F 19/24* (2013.01); *G01N 2021/6415* (2013.01); *G01N 2201/06113* (2013.01); *G01N 2201/12* (2013.01)

(56) References Cited

U.S. PATENT DOCUMENTS

| | | |
|---|---|---|
| 2003/0134320 A1 | 7/2003 | Barrus et al. |
| 2004/0195101 A1 | 10/2004 | Sharaf et al. |
| 2006/0058969 A1 | 3/2006 | Liao et al. |
| 2006/0102479 A1 | 5/2006 | Sharaf et al. |
| 2007/0202526 A1 | 8/2007 | Nakami et al. |
| 2008/0154517 A1 | 6/2008 | Barrus et al. |
| 2009/0182512 A1 | 7/2009 | Matsumoto et al. |
| 2009/0226916 A1 | 9/2009 | DeSimas et al. |
| 2010/0096548 A1 | 4/2010 | Sharaf et al. |
| 2011/0008785 A1 | 1/2011 | Tan et al. |
| 2011/0256631 A1* | 10/2011 | Tomaney .......... C12Q 1/6869 436/94 |
| 2013/0084572 A1* | 4/2013 | Hindson .......... G01N 21/6428 435/6.12 |

FOREIGN PATENT DOCUMENTS

| | | |
|---|---|---|
| JP | 2006-017461 A | 1/2006 |
| JP | 2006-084471 A | 3/2006 |
| JP | 2007-259847 A | 10/2007 |
| JP | 2008-250401 A | 10/2008 |
| JP | 2012-529908 A | 11/2012 |
| WO | 2013/040583 A2 | 3/2013 |
| WO | 2014/097888 A1 | 6/2014 |

* cited by examiner

NUCLEIC ACID ANALYZER AND NUCLEIC ACID ANALYSIS METHOD USING SAME

TECHNICAL FIELD

The present invention relates to nucleic acid analyzers for simultaneously detecting a sample labeled in multiple colors and nucleic acid analysis methods using the analyzer, and, more particularly, to a nucleic acid analyzer for detecting DNA, proteins, or the like and a nucleic acid analysis method using the analyzer.

BACKGROUND ART

Analyzers used for speedy identification (namely, nucleic acid sequence analysis, base length analysis of a characteristic genomic sequence, or the like) of various species of organisms such as human, animals, plants, bacteria, and viruses include, for example, Applied Biosystems 3500 Series Genetic Analyzers (Life technologies Corp.) using a capillary electrophoresis method.

Also, development of devices and techniques for fully integrated (namely, integrated from inputting a sample to outputting a result) target nucleic acid analysis is ongoing for easier analysis.

An analytical technique for a target nucleic acid sequence allows an end user to make determination in a clinical test, forensic judgment, etc. For example, a large part of general diseases of human can be determined based on DNA sequence base pairs of less than about 1000 bases being as a target site without involvement of analysis on the whole human genome. Similarly, an accurate measurement in base length analysis of about twenty characteristic genomic sequences formed in short tandem repeat analysis (hereinafter referred to as STR analysis) is more in use for identifying a given individual.

Therefore, target nucleic acid analysis can be performed on site under various conditions including a laboratory of a university or hospital, at bedside of a patient, forensic judgment, or environment measurement depending on an object of the analysis. However, performing the analysis involves complicated manual adjustment of a sample and data analysis by a researcher or the like with expertise.

Therefore, as an example of a scheme to reduce the expertise requirement and to make analysis easier, a method for efficiently interpreting double peaks due to a hetero junction, which are difficult to interpret, in a base sequence analysis using a DNA sequencer is disclosed (refer to PTL 1). This is a method for performing sequence analysis of maternally and paternally derived polymorphism with a double-detected chromatogram in a base sequence analysis based on a setting prepared in advance.

CITATION LIST

Patent Literature

PTL 1: JP 2006-84471 A

SUMMARY OF INVENTION

Technical Problem

The method descried in PTL 1 is useful when sequence analysis is performed on polymorphism in hetero junction. However, if not in sequence analysis but in STR analysis where multiplexed polymerase chain reaction (PCR) is performed and fluorescence in multiple colors (five to six colors) is detected, it is assumed that a true signal may be detected in multiple colors at the same timing irrelevant to a relative ratio of peak heights.

In PTL 1, however, removal of a false signal due to a pull-up peak is not considered. Therefore, incorrect analysis may be performed due to the pull-up peak and thus a problem remains that a true peak to be analyzed may be removed. That is, this results in a constraint that, for analysis with high accuracy, an operator with expertise has to perform the analysis.

Furthermore, apart from the aforementioned example, there is a case where data analysis has to be performed by an operator with expertise as in the following examples.

For example, STR analysis is performed with amplification (multiplexed PCR) targeting on multiple sequence sites inmost cases. In such an analysis, generally, a concentration of genome DNA extracted from a biological sample is specified and multiplexed PCR is performed within the specified range, thereby conducting electrophoresis. The number of repetitions is then analyzed from signals acquired and, for example, an individual is identified. In such analysis of signals, there are problems such as irregular balance of peak heights of alleles or a signal lower than a detection threshold when the amount of genome DNA is too small.

Also, when sample genome is in excess, there may be artifacts including increased stutters, generation of non-specific band, addition of incomplete non-templates, and a pull-up peak. These phenomena may lead to misinterpretation of an STR profile.

There is another problem that an influence of crosstalk due to parallel detection of signals has to be also considered upon analysis of multiple samples.

(1) Therefore, a nucleic acid sequence analysis and a base length analyzer for a characteristic genomic sequence, which are easy to use and do not require an operator with expertise such as a researcher, are desired. For example, a system where all manual processes are omitted is on demand. As an effect, less training is required. An individual forced to be in a difficult environment that a first responder such as a nurse or police officer may encounter can easily operate the analysis system.

Other than reduced requirement on expertise as described above, the improvements listed below are desired for nucleic acid sequence analysis or base length analysis of a characteristic genomic sequence.

(2) An analysis system providing a speedy analysis result is desired. For clinical use such as sequencing of a contagium for determining an appropriate treatment in a hospital or the like, to perform a treatment of antibacterial and antivirus pharmacotherapy in a short time after arrival of an urgent patient, analysis in a short time (e.g. within 90 minutes) is required. Desirable time to obtain a result for identification of an individual in initial investigation of the police is sufficiently shorter (e.g. within 90 minutes) than a few days to several weeks as achieved by the conventional art. Without being limited to the above use, data analyzable in a short time needs to be formed. Furthermore, speedy analysis may advantageously result in increased sample throughput at the same time.

(3) Downsizing the analyzer is desired. Most of nucleic acid sequence analysis systems require the entire laboratory and related support. Nucleic acid sequence analysis systems with high throughput such as MiSeq (illumina, Inc.), ion-trrent PGM (Life technologies Corp.), and FLX (Roche Diagnosis Corp.) that have been in market recently only require a simple desk for installation. However, a large analysis facility is required for sample preparation required for the analysis. For example, sequence analysis or STR analysis generally requires a facility for sample preparation such as extraction of genome DNA from a biological sample, concentration adjustment, amplification of a target site by a nucleic acid amplification method, or adjustment of an analysis library. Therefore, downsizing is important for both use in a laboratory and treatment site and on-site operation. Downsizing is also an important problem for reducing cost per sample.

Therefore, an object of the present invention is to provide a nucleic acid analyzer which is easy to use, small-sized, capable of accepting multiple samples, and performs speedy analysis and a nucleic acid analysis method using the analyzer.

Solution to Problem

In order to solve the aforementioned problems, a nucleic acid analysis method according to the present invention has main characteristics as follows.

(1) The nucleic acid analysis method includes a step of irradiating, with light, an analysis sample including a plurality of DNA fragments, a step of detecting fluorescence, excited from the analysis sample, corresponding to the DNA fragments with an imaging element within a predetermined detection time, a step of setting a lower limit of fluorescence intensity required for analysis of the analysis sample within a detectable range of fluorescence intensity of the imaging element, a step of acquiring fluorescence intensity for each of the DNA fragments based on the lower limit, a step of detecting a peak of the fluorescence intensity acquired for each of the DNA fragments and determining time information corresponding to the peak, and a step of displaying correspondence of the fluorescence intensity to the time information for each of the DNA fragments. The display displays at least one or more peaks including a first peak having first fluorescence intensity and a second peak having fluorescence intensity weaker than the first fluorescence intensity. The lower limit is adjusted with a predetermined value and fluorescence intensity, where measurement is made using the adjusted lower limit as the lower limit of the imaging element, is reset as fluorescence intensity of at least one or more peaks including the second peak, thereby determining whether at least one or more peaks including the second peak are false signal peaks.

Also, a nucleic acid analyzer according to the present invention has main characteristics as follows.

(2) The nucleic acid analyzer includes a light irradiating unit for irradiating, with light, an analysis sample including a plurality of DNA fragments, a detecting unit for detecting fluorescence intensity, excited from the analysis sample, corresponding to the DNA fragments with an imaging element within a predetermined detection time, a storage for storing a lower limit of fluorescence intensity required for analysis of the analysis sample within a detectable range of fluorescence intensity of the imaging element, an arithmetic control unit for controlling the respective units and performing arithmetic processing, and a display unit for displaying a result from the arithmetic control unit. The detecting unit acquires fluorescence intensity for each of the DNA fragments based on the lower limit. The arithmetic control unit detects a peak of the fluorescence intensity acquired for each of the DNA fragments and determines time information corresponding to the peak. The display unit displays correspondence of the fluorescence intensity to the time information for each of the DNA fragments. The display unit displays at least one or more peaks including a first peak having first fluorescence intensity and a second peak having fluorescence intensity weaker than the first fluorescence intensity. The arithmetic control unit adjusts the lower limit with a predetermined value, resets fluorescence intensity, where measurement is made using the adjusted lower limit as the lower limit of the imaging element, as fluorescence intensity of at least one or more peaks including the second peak, and thereby determines whether at least one or more peaks including the second peak are false signal peaks.

Advantageous Effects of Invention

The present invention provides a nucleic acid analyzer which is easy to use, small-sized, capable of accepting multiple samples, and performs speedy analysis and a nucleic acid analysis method using the analyzer.

DESCRIPTION OF EMBODIMENTS

Embodiments of the present invention will be described below with reference to the drawings.

<<Capillary Electrophoresis Device>>

Figure 1:
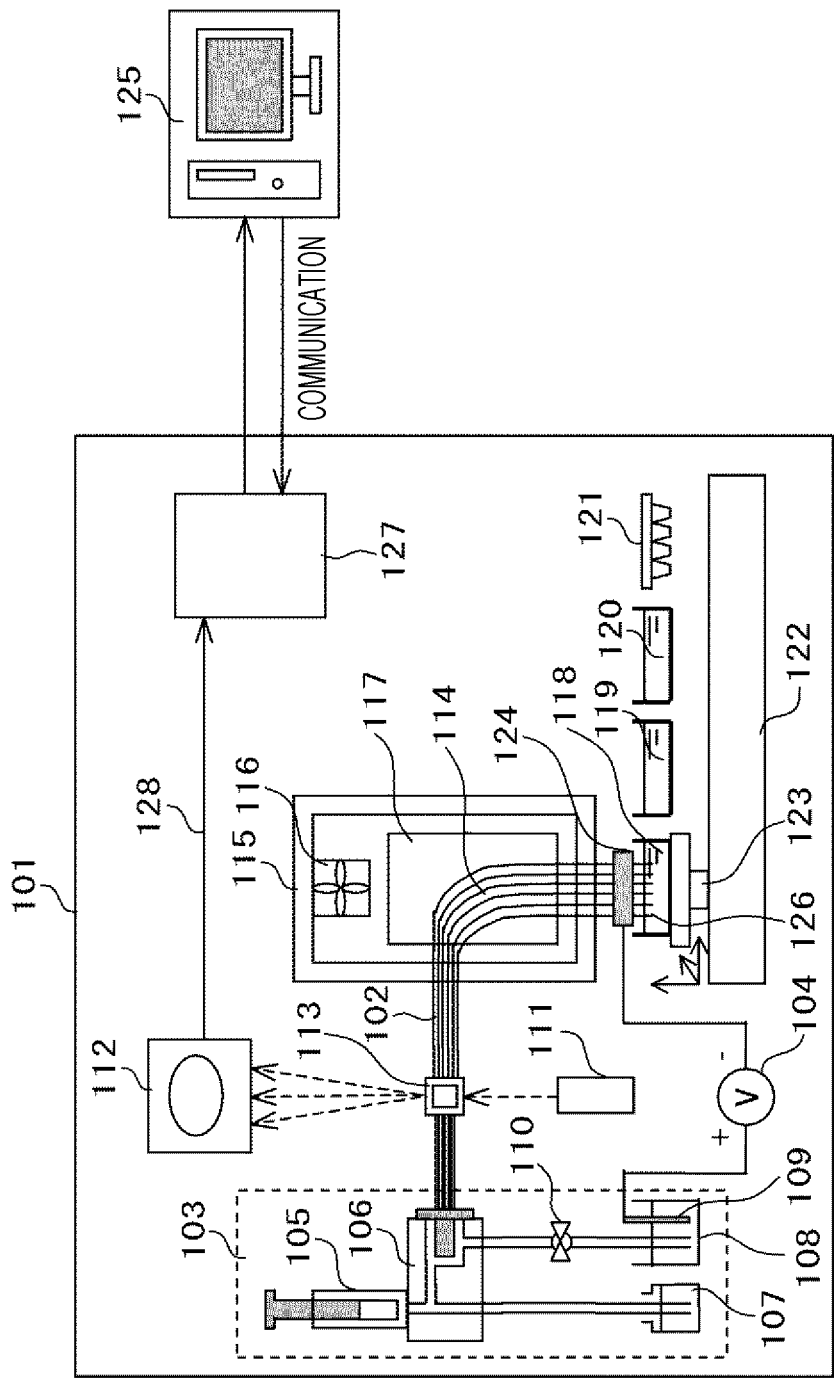
FIG. 1 is a schematic diagram illustrating a capillary electrophoresis device according to the present embodiment.

FIG. 1 is a schematic diagram illustrating a capillary electrophoresis device according to the present embodiment. A configuration of the device will be described below with reference to FIG. 1.

A device main body 101 is connected to a control computer 125 via a communication cable. An operator controls respective functions of the device by the control computer 125 and receives data detected by an optical detector 112. The control computer includes a data display screen (not shown) for displaying received data.

The capillary electrophoresis device according to the present embodiment includes a capillary array 114 including one or more capillaries 102 containing separation medium for separating an analysis sample adjusted in advance, a conveyor 122 for conveying various analysis containers to a capillary cathode edge 126, a pump mechanism 103 for injecting the separation medium into the capillaries, a thermostatic chamber 115 for adjusting temperature of the capillary array, a high voltage power supply 104 for applying high voltage to the separation medium, a light source 111 for irradiating the capillaries with a coherent laser beam, and an optical detector 112 for optically detecting fluorescence emitted from the sample.

The capillary array 114 is a replaceable member having one or more (e.g. 2 to 96) capillaries 102 and includes a load header 124, a detecting unit 113, and a capillary head. An edge of the capillary array 114 includes a load header 124 for introducing the analysis sample into the capillaries and forms a cathode edge where negative voltage is applied. On the other edge, the plurality of capillaries is bound together by the capillary head and connected to a gel block 106 in a pressure-resistant airtight structure. The detecting unit 113 where the laser beam is irradiated is disposed between the load header 124 and the capillary head.

The capillary array 114 can be replaced with another array having capillaries of a different number or with a different length depending on measurement. Also, when there is a damage or deterioration of quality in the capillary, the capillary array is replaced with a new one.

The capillary 102 is a glass tube with an internal diameter of several tens to hundreds micrometers and an external diameter of several hundreds micrometers. A surface of the capillary is covered with polyimide coating for improved strength. In a part irradiated with the laser beam and vicinity thereof; however, the polyimide coating on the capillary surface is removed. The inner part of the capillary is filled with the separation medium for separating DNA molecules in the analysis sample. The separation medium includes, for example, polyacrylamide-based separation gel (hereinafter referred to as polymer) commercialized by multiple companies for electrophoresis. Note that a supporting member of the separation medium is exemplified by the capillary made of glass tube, etc. in the embodiment, but is not limited thereto. A glass substrate or resin substrate of microfluidics may be used.

The pump mechanism 103 includes a syringe 105 and a mechanical system for pressuring the syringe. The gel block 106 is a connecting part connecting each of the syringe 105, the capillary array 114, an anode buffer container 108, and a polymer container 107. When filling the capillary with the polymer, which is the separation medium, closing an electric valve 110 and pushing the syringe 105 allow the polymer inside the syringe 105 to be injected into the capillary.

A thermostatic chamber 115 is a temperature control mechanism for controlling temperature of the capillary array 114. The thermostatic chamber 115 is covered with a heat insulator for keeping the temperature inside the chamber constant. The temperature is controlled by a heating and cooling mechanism 117. This allows for keeping the temperature of the most part of the capillary array constant such as at 60° C.

The conveyor 122 includes three electric motors and linear actuators, and thus is made movable in directions of three axes of up and down, left and right, and front and rear. Also, a moving stage 123 of the conveyor 122 can be mounted with at least one or more containers. The conveyor 122 conveys each of a buffer container 118, a washing container 119, a waste liquid container 120, and a sample container 121 on the moving stage 123 to the cathode edge 126 of the capillaries.

An optical detecting unit includes an irradiation system having the light source 111 for irradiating the detecting unit 113 with excitation light and the optical detector 112 for detecting emission from the detecting unit 113. Data 128 detected by the optical detector 112 is transferred to the control computer 125 via a control substrate 127. In the optical detecting unit, a diffraction grating or prism may be used for spectroscopy and an imaging element such as CCD or CMOS may be used thereafter for optical detection. Alternatively, optical detection may be performed by a combination of a plurality of dichroic mirrors and a photo multiplier.

<<Irradiation System>>

Figure 2:
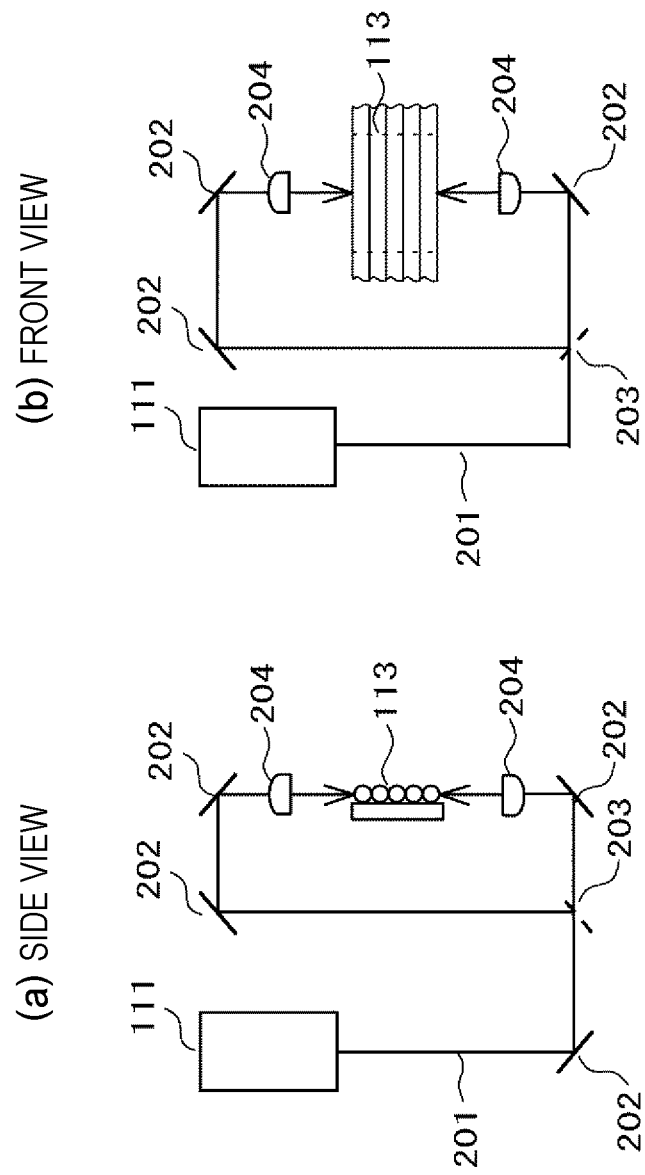
FIG. 2 is a schematic diagram illustrating an irradiation system according to the present embodiment.

In FIG. 2, a schematic diagram of an irradiation system according to the present embodiment is illustrated. FIG. 2(a) is a side view and FIG. 2(b) is a front view. The irradiation system includes the light source 111 for oscillating a laser beam 201, a beam splitter 203 for splitting the laser beam, a reflection mirror 202 for changing a traveling direction of the laser beam, a condenser lens 204 for condensing the laser beam on the detecting unit 113 of the capillary array. Note that optical elements such as a filter, polarizer, and wavelength plate are omitted herein for simplification. The laser beam 201 oscillated from the light source 111 changes traveling direction thereof when reflected by the reflection mirror 202 and is split into two beams by the beam splitter 203. The capillaries in the detecting unit 113 are irradiated, from above and bottom, with the two beams via the reflection mirror 202 and condenser lens 204. Observing fluorescence emitted from the detecting unit by the optical detector 112 allows for detecting a signal of the pretreated sample.

The light source 111 emits excitation light for exciting a sample component. The light source 111 may be a liquid laser, gas laser, or semiconductor laser as appropriate. An LED may be alternatively used. The light source 111 is, for example, a semiconductor laser with a wavelength of 515.5 nm and an output of 50 mW. An excitation wavelength is dependent on pretreated fluorescence. Wavelengths of 505 nm, 488 nm, 532 nm, or 633 nm may also be used as appropriate.

Furthermore, irradiation of the capillary array 114 may be variable as appropriate by irradiating only one side of the capillary array with the excitation light, varying lighting time of the light source, or providing a shutter on the optical axis. Irradiation of the capillaries with the excitation light may be performed by, for example, repeating irradiation for 50 msec and data transfer (no irradiation performed during data transfer) as one set of irradiation conditions or repeating irradiation for 50 msec, data transfer, irradiation for 100 msec, and data transfer as one cycle of irradiation conditions. This results in smaller fluorescence signal data scores acquired under the above conditions having one irradiation time; however, fluorescence signal data with irradiation for 100 msec is also acquired, thereby expanding a detection range of fluorescence signals. This expansion of the detection range results in a great effect. In analysis by a researcher or the like, it was required to adjust an amount of genome DNA in advance within a detection range of an electrophoresis device.

If it is not required to adjust an amount of genome DNA in advance as a result of the expanded detection range as described above, operation by a researcher is no longer required. The analyzer is also no longer required to have a concentration adjustment function, thereby allowing a speedy, downsized, and reasonable device to be provided.

<<Operation Procedure of Electrophoresis Device>>

Figure 3:
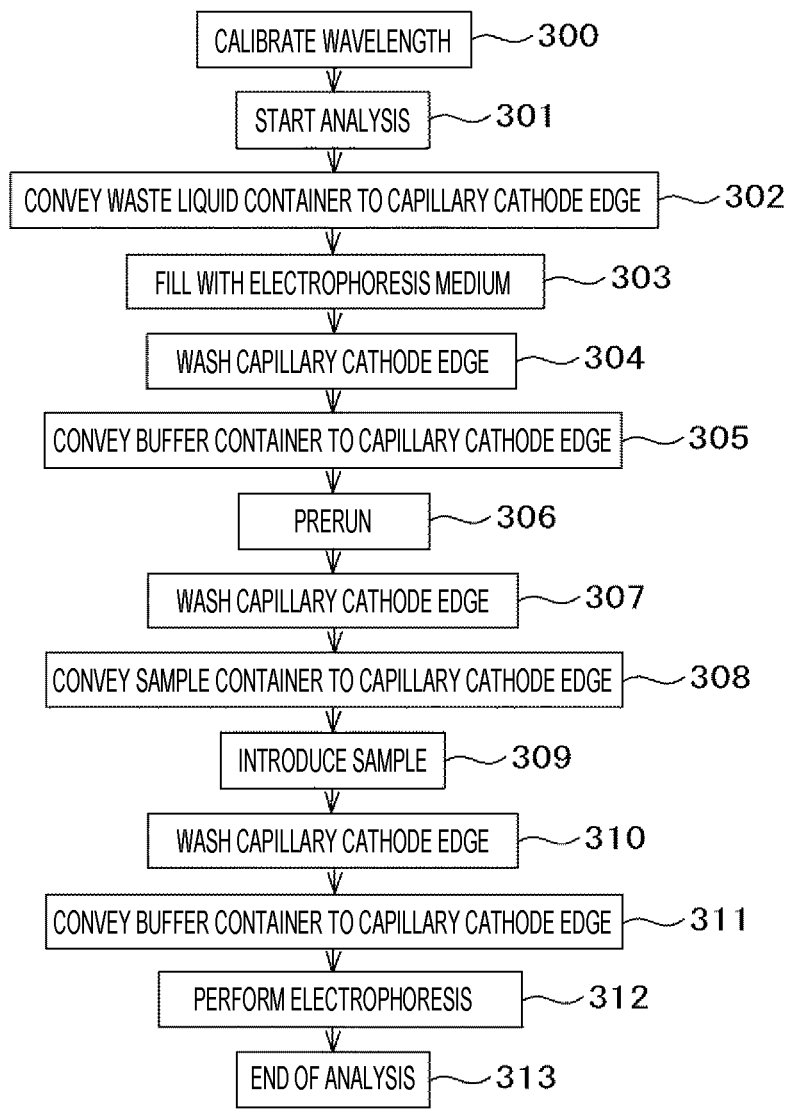
FIG. 3 is a flow chart illustrating an analysis procedure of electrophoresis.

First, a basic operation procedure of the electrophoresis device will be described. As shown in FIG. 3, the operation procedure includes preparation, filling with electrophoresis medium 303, prerun 306, sample injection 309, and electrophoresis 312 in the order mentioned.

Next, the aforementioned preparation will be described. An operator of the device installs, in the device, the buffer container 118 containing electrophoresis buffer, the washing container 119 for washing the capillaries, the waste liquid container 120 for receiving discharged polymer from the capillaries, the polymer container 107 containing polymer that is separation medium, and the sample container 121 containing a sample to be measured.

Figure 8:
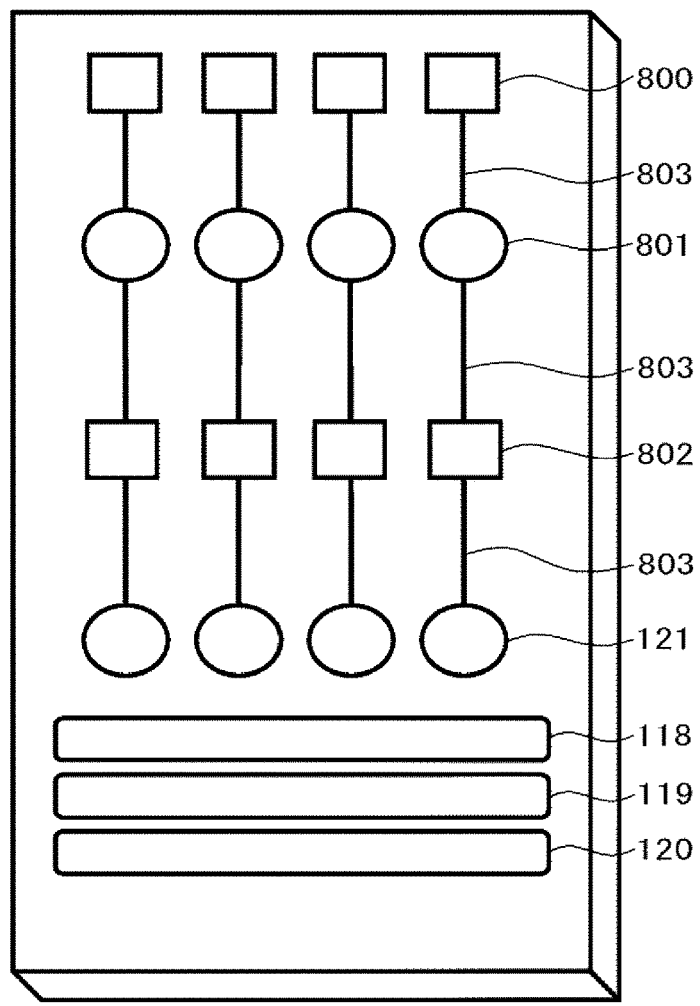
FIG. 8 is a schematic diagram illustrating a reaction container according to the present embodiment.

Note that a reaction container as illustrated in FIG. 8 where the buffer container 118, washing container 119, waste liquid container 120, and sample container 121 are combined into one integrated container may be used and installed for ease of operation by the operator.

The reaction container as illustrated in FIG. 8 may be used in amplification of genome DNA. A structure may be employed where liquids such as reagents in the respective parts are fed by the principal of diaphragm while using an elastic body such as rubber in the bottom part of the container. Genome DNA is placed in a sample addition vessel 800 and transferred to an amplifying reagent vessel 801 containing nucleic acid amplifying reagent used for isothermal amplification reaction such as RCR reaction, the LAMP method, or the NASBA method, which are a nucleic acid amplification methods using DNA polymerase or the like. The amplification method is not limited to the above. After the sample transferred is mixed well, the mixed liquid is then transferred to a reaction vessel 802 having a temperature adjusting function and a target nucleic acid sequence is amplified. The amplification product is transferred to the sample container part 121.

Also, before measurement, all passages including the capillaries used for electrophoresis are filled with the polymer using the pump mechanism 103. Note that, in a case of continuous use of the device, this step is not required since the passages are filled with the polymer.

<<Procedure of Electrophoresis Analysis>>

Procedure of electrophoresis (steps (1) to (14)) will be described below with reference to FIGS. 1, 3, 4, and 8.

(1) Step 300: First, perform wavelength calibration before analysis of any sample. In the wavelength calibration, detection of a fluorescence signal is performed by the optical detector 112. When, for example, a CCD is used as the optical detector 112, an element part corresponding to each fluorescence wavelength is designated for detection. The optical detector 112 is set such that each of a plurality of fluorescent dyes diffracted by a diffraction grating or the like is detected with the highest sensitivity.

Figure 4:
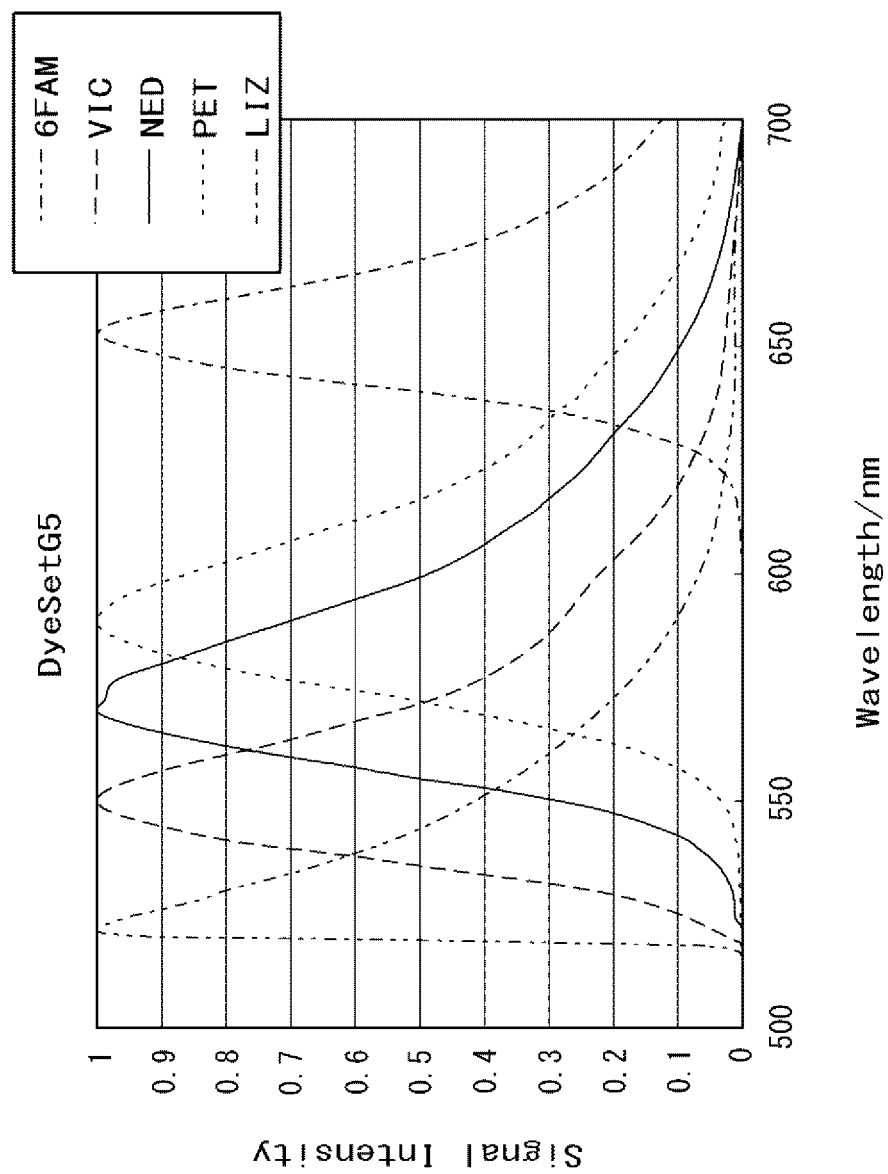
FIG. 4 is a diagram illustrating an example of emission spectra of fluorescent dyes.

Such fluorescent dyes may be exemplified by fluorescent dyes of AmpFLSTR Kit (Life Technologies Corp.) including fluorescent dyes called 6FAM, VIC, NED, PET, and LIZ. An emission spectrum of each of the fluorescent dyes is illustrated in FIG. 4. The emission spectrum of each of the fluorescent dyes has a broad pattern as illustrated in FIG. 4.

For example, a CCD element for detecting a sample labeled with NED receives signals including those from fluorescence with a wavelength other than that of NED even though there is a difference in intensity. Furthermore, the fluorescence emitted from NED is also detected in another element, other than the target element, for detecting another wavelength. However, since a ratio of signal intensity of each of the fluorescence is theoretically constant, inverse transformation based on this value should give a peak waveform attributable solely to the target fluorescence wavelength. This applies to fluorescent dyes with other wavelengths and thus a waveform detected is assumed to be a simple sum of spectra where a fluorescence spectrum overlaps with another fluorescence spectrum.

Therefore, when ratios of signal intensity for the plurality of fluorescent dyes are available, expressing them in a matrix and multiplying an originally detected peak waveform with an inverse matrix thereof results in peak waveforms of the respective fluorescent dyes. This ratio of signal intensity can be obtained in advance by electrophoresis using a calibration sample or the like (e.g. refer to Japanese JP 2002-525576 W, JP 2011-30502 A, or JP 2002-78500 A) Note that this operation (calculation of matrix coefficients) is generally performed every time the capillary is replaced due to deterioration or change of length.

(2) Step 301: The device initiates analysis upon a command, by the operator, from the control computer 125.

(3) Step 302: First, the waste liquid container 120 is conveyed to the capillary cathode edge 126 by the conveyor 122.

(4) Step 303: The pump mechanism 103 then injects the polymer into the multi-capillary array 114 (filling with electrophoresis medium).

(5) Step 304: After completion of injection of a predetermined amount of polymer, the washing container 119 is conveyed to the capillary cathode edge 126 by the conveyor 122, where the capillary cathode edge is washed while being soaked in solution.

(6) Step 305: After the capillary is washed, the buffer container 118 is conveyed to the capillary cathode edge 126 by the conveyor 122.

(7) Step 306: Thereafter, prerun is performed. The prerun is performed before the main analysis steps, thereby making the polymer within the capillary in a suitable condition for analysis. Normally, voltage of a few to several tens kilovolts is applied for a few to several tens minutes.

(8) Step 307: After completion of the prerun, the capillary cathode edge 126 is washed again in the washing container 119.

(9) Step 308: The sample container 121 is conveyed to the capillary cathode edge.

(10) Step 309: Next, applying voltage of a few kilovolts to the capillary cathode results in generation of electric field between the sample solution and an anode electrode 109 and a sample in the sample solution is introduced into the capillary.

(11) Step 310: After introduction of the sample, the capillary cathode edge 126 is washed again in the washing container 119.

(12) Step 311: The buffer container 118 is conveyed to the capillary cathode edge 126.

(13) Step 312: Thereafter, a predetermined voltage is applied and electrophoresis is initiated.

Here, electrophoresis is to cause a sample in a capillary to have mobility by an action of electric field generated between the cathode and anode buffers and to separate the sample using a difference in mobility dependent on a property of the sample. When the sample is DNA, mobility depends on a base length. DNA with shorter base length and thus with higher mobility passes the detecting unit earlier. Since DNA is attached with a fluorescent material in advance, DNA with shorter base length is optically detected by the detecting unit earlier. Normally, measurement time and voltage applying time are set according to a sample having the longest migration time.

(14) Step 313: When a predetermined time elapses from initiation of voltage application, data is acquired and then voltage application is halted to finish the analysis. The above is the basic procedure of electrophoresis.

<<General STR Analysis Procedure>>

Figure 5:
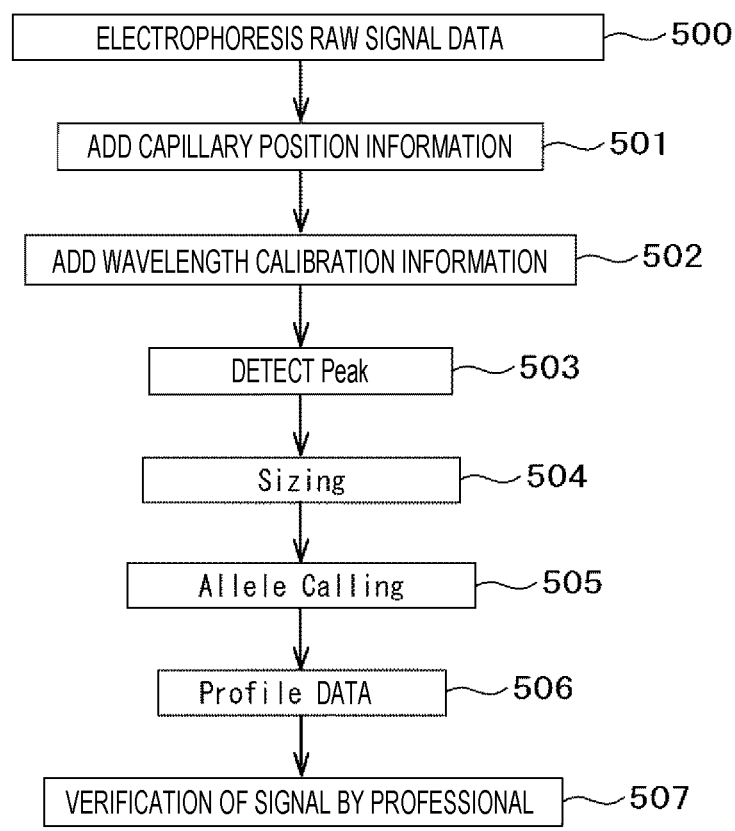
FIG. 5 is a flow chart illustrating an STR analysis procedure.

Next, an analysis procedure of a general STR analysis will be described with reference to FIG. 5.

(1) Step 500: Acquire signal data by electrophoresis.

(2) Step 501: Add capillary position information, within a detector 112, having been acquired in advance.

(3) Step 502: Further add wavelength calibration information 300.

Steps 503 to 505 below correspond to STR analysis processing.

(4) Step 503: Extract only target signals. Information such as detection time, height, and width of each peak is calculated from the signals (peak detection).

(5) Step 504: Perform sizing of an analysis sample based on information acquired in step 503 and peak detection information where a DNA fragment of a known size is also subjected to electrophoresis simultaneously with the sample (sizing).

(6) Step 505: With this information of sizing, association is established with advance information of an allele of the analysis target (allele calling).

(7) Step 506: Calculate a base length or the number of repetitions of a sequence and obtain profile data.

(8) Step 507: A specialist verifies this profile data and interprets the data based on knowledge and experience.

<<STR Analysis Procedure According to the Present Application>>

Next, an STR analysis procedure using the electrophoresis device according to the present invention will be described with reference to FIG. 6. Note that the general STR analysis procedure has been described in FIG. 5 while in FIG. 6 an analysis procedure according to the present invention will be described. Especially, a procedure different from that in FIG. 5 includes steps 600 to 602 and 608 to 609 in FIG. 6. The above procedure allows for analysis which is easy to use and does not require an operator with expertise such as a researcher.

Although an STR analysis procedure is described below, the present analysis procedure is not limited thereto but also applicable to DNA base sequence analysis.

(1) Step 600: First, a signal analysis condition is set. A device manufacturer or administrator sets the condition in advance, thereby allowing interpretation of profile data to be performed in a speedy manner as a routine work and not by a professional.

Here, to be noted is interpretation of a false peak. Most of the false peaks can be attributed to a noise peak attributable to hardware such as a dark current in device optics, a peak carried over from a sample used in a previous analysis, a crosstalk peak due to faint leakage when a plurality of capillaries is included in the detecting unit, a pull-up peak that slightly appears even after matrix transformation by calculation of matrix coefficients, or a peak attributable to a stutter, which is an unwanted amplified object resulted from a nucleic acid amplification method. A specialist interpreting data performs analysis by setting a fixed threshold based on earlier experience or determines a false peak from a profile pattern obtained.

Figure 7:
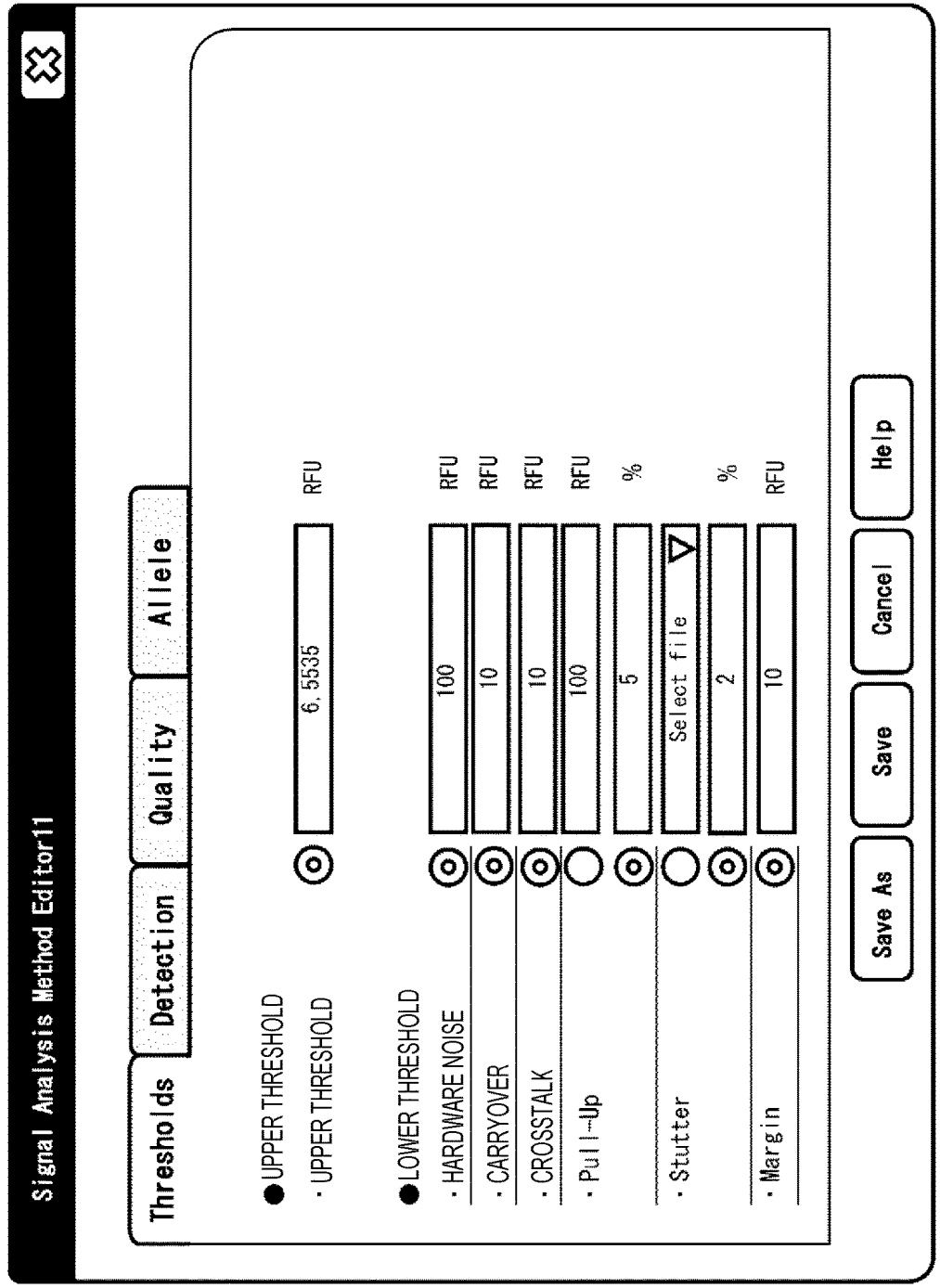
FIG. 7 is a diagram illustrating an exemplary input screen of a control computer according to the present embodiment.

On the contrary, in the present embodiment where analysis by an expertise is not required, conditions for automatic interpretation of false peaks are first set in a condition setting screen for signal analysis as illustrated in FIG. 7. A provider of the device or a user of the analysis can make various settings.

A screen illustrated in FIG. 7 is used for setting thresholds (upper threshold and lower threshold) for signals acquired. For the upper threshold, an upper detection limit of the detector may be set. Alternatively, a value where linearity can be obtained from a faint signal to strong signal may be set in order to maintain quantitativeness of signals acquired. Setting items for the lower threshold include hardware noise, carryover, and crosstalk. It is desirable that these items defined by a manufacturer well versed with the performance of the device. An operator of the device may change these values, based on values recommended by the manufacturer, according to an analysis condition, use condition, or an environment.

Next is a setting item for a pull-up peak. A setting method may include two options as described below. One option is to measure and evaluate, in advance, a pull-up peak under a use condition and to set a fixed value as device performance. The other option is to set a ratio to a parent peak of the pull-up. A pull-up is greatly dependent on signal intensity of another wavelength acquired at the same timing upon detection. From this correlation, constantly calculating a ratio to a signal of another wavelength (parent peak) acquired at the same timing as a pull-up peak, which is a false peak, allows for removing false peaks. When there are a plural number of parent peaks, the calculation can be performed for each wavelength. Also, the calculated values may be summed up to obtain the pull-up peak. It is desirable that these ratios are evaluated in advance in a similar manner to setting the fixed value. The pull-up peak is dependent on a device, further on a detection system, amplifying reagent, and matrix transformation by matrix calculation. Therefore, the advance evaluation may be performed each time one of these factors is changed before changing the setting value. Also, the threshold may be changed depending on an analysis method such as nucleic acid sequence analysis or short tandem repeat analysis.

Alternatively, since the reaction container illustrated in FIG. 8 is integrated with amplifying reagent, the above information may be added to a bar code attached to the reaction container, thereby allowing the device to acquire a ratio dependent on the reagent.

When ratios of signal intensity for the plurality of fluorescent dyes in reagent used for analysis are available, expressing them in a matrix and multiplying an originally detected peak waveform with an inverse matrix thereof results in waveforms of the respective fluorescent dyes. The advance evaluation refers to obtaining this ratios of signal intensity in advance by performing electrophoresis with a calibration sample or the like. Also, the ratio of signal intensity may be automatically reflected to the setting item for pull-up peak after electrophoresis using the calibration sample.

Next is an item for a stutter. A setting method may include two options as described below. One option is to obtain a false peak value attributable to a stutter for each allele from information acquired in advance from a providing company of the reagent or a user on obtained signals attributable to the stutter in relation to each allele peak (e.g. a ratio of the peak to the allele). The other method is to set a fixed value. As for the stutter, a spot where a peak appears can be estimated, and thus it is possible to set a condition, from the advance information, where an influence of the stutter is not considered when an allele peak is not adjacent thereto. As for the lower thresholds, a sum of the values set here gives a basic lower threshold for determination on a signal acquired by the detector. Signals are analyzed according to the threshold acquired from settings of the aforementioned items.

Other items for analysis as illustrated in FIG. 7 includes, for example, "Detection" in a tab illustrated. A signal acquired by the detector is information on a point where fluorescence intensity and detection time are specified. In order to make a peak recognizable as a continuation of this point information, various methods for performing curve fitting are set such as polynomial approximation.

In item "Quality" in a tab illustrated, a quality of the peak obtained by the curve fitting or the like is checked. According to conditions set here, whether the peak obtained is desirable is determined. Items for quality check include determination on whether a half width is larger than a certain width. If the half width is larger than the certain width, there is a possibility that the peak is too broad to correctly perform sizing.

An example of item "Allele" in a tab illustrated is determination on whether allele peaks acquired are heterozygous when intensity of one peak has a certain intensity in relation to intensity of the other peak. Other setting items include setting the number of peaks that are obtained adjacent to alleles. Usually, one or two peaks are obtained. Therefore, a value may bet set for clearly showing an analysis result when other number of peaks are obtained.

Signal analysis condition settings (600) includes the above items, but not limited thereto.

(2) Step 601: As a next step, reagent information is read. Here, FIG. 8 illustrates a reaction container, containing amplifying reagent or the like, installed in the device. Specifically, the device includes the sample addition vessel 800, amplifying reagent vessel 801, reaction vessel 802, and sample container 121.

When installing the reaction container, containing amplifying reagent or the like, as illustrated in FIG. 8 to the device, reaction efficiency differs depending on a storage period of the reaction container. For example, activity of DNA polymerase used for nucleic acid amplification decreases as a storage period becomes longer. With a container with a short storage period and a container with a long storage period, both added with the same sample, different signal intensities are acquired, and thus the detector is required to have a wider dynamic range.

Recording a manufacturing date of the reagent in a bar code or the like upon manufacturing the reaction container and allowing the device to read the bar code or the like after installment of the reaction container allows the device to obtain storage status of the reagent. A temperature condition in the amplification step is determined considering this information, activity information on the reagent having been researched in advance, and information on the dynamic range of the detector. If the amplification reaction is PCR reaction, the number of temperature cycles is increased or decreased. If the isothermal amplification method is used, reaction time is increased or decreased. Adjusting a temperature condition allows for obtaining desirable signal intensity. Therefore, a wide dynamic range is no longer required.

(3) Step 602: Next, electrophoresis is performed.

It is desirable that irradiation with excitation light in electrophoresis is variable as appropriate. Acquiring signals in a plurality of exposure times allows for increasing a range of signal intensity detectable by the detector. Therefore, a detector with a wide dynamic range is not required, thereby allowing for easy analysis at a reasonable cost. Also, adjustment of genome DNA concentration is not required and thus a speedy and simple device can be implemented.

(4) Step 603: Acquire data by electrophoresis.

(5) Step 604: Add capillary position information, within a detector 112, having been acquired in advance.

(6) Step 605: Further add wavelength calibration information (605).

(7) Step 606: Extract target signals only. Information such as detection time, height, and width of each peak is calculated from the signals (peak detection).

(8) Step 607: Perform sizing of an analysis sample based on this information and peak detection information where a DNA fragment, labeled with fluorescence, of a known size is also subjected to electrophoresis simultaneously (sizing).

(9) Step 608: Next, compare detection times of signal peaks in respective colors acquired in respective wavelength ranges. When peaks are detected in the same sample in the same detection time but at different detection wavelengths, a lower threshold for one of the peaks is changed based on fluorescence intensity of the parent peak and a value having been set in the signal analysis condition settings (600).

Figure 9A:
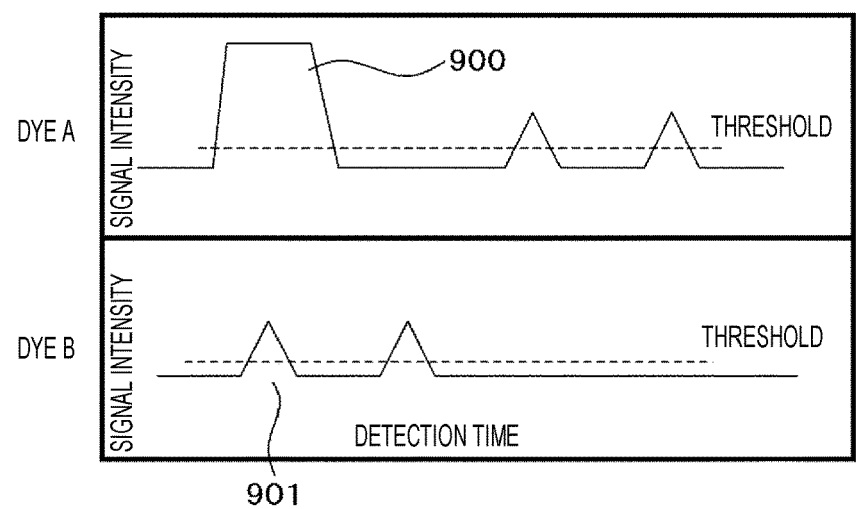
FIG. 9A is a diagram illustrating an exemplary signal waveform showing effects of the present embodiment.
Figure 9B:
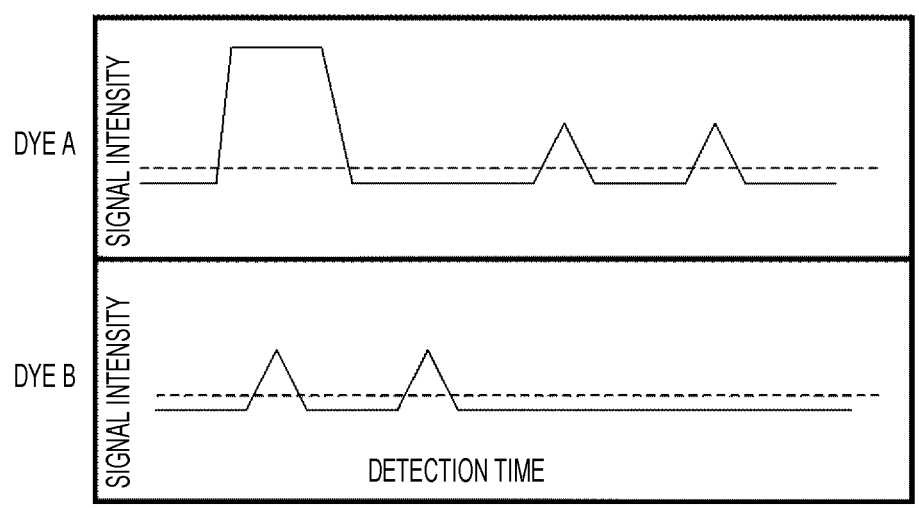
FIG. 9B is a diagram illustrating an exemplary signal waveform showing effects of the present embodiment.
Figure 9C:
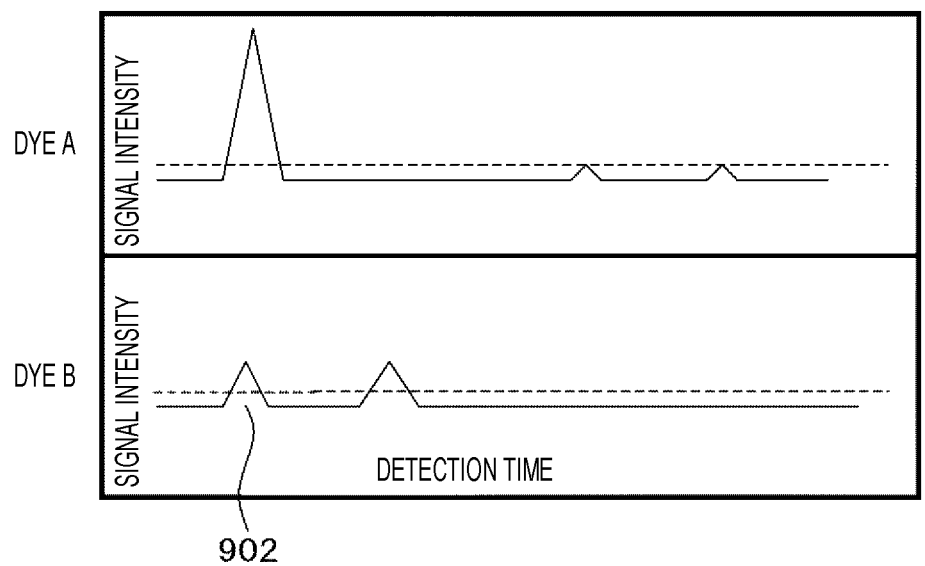
FIG. 9C is a diagram illustrating an exemplary signal waveform showing effects of the present embodiment.

Here, an example where signals are detected in short and long exposure times with reference to FIGS. 9A to 9C. For lower threshold factors dependent on exposure time, a lower threshold thereof is changed according to length of the exposure time. For example, hardware noise is dependent on exposure time. The longer exposure time is, the larger hardware noise is, and vice versa. FIG. 9A illustrates data where signals are acquired with only one exposure time. A sample added with dye A provides data where signals saturated (900) and thus a peak height cannot be analyzed. Therefore, a pull-up peak cannot be calculated and thus whether a peak obtained with dye B (901) is attributable to a pull-up or to the sample cannot be determined.

However, detection in long and short exposure times as illustrated in FIGS. 9B and 9C allows for detecting a peak height from data detected in the short exposure time even when signals saturate as in FIG. 9B. Here, FIG. 9B illustrates a case of the long exposure time and FIG. 9C illustrates a case of the short exposure time.

Figure 9D:
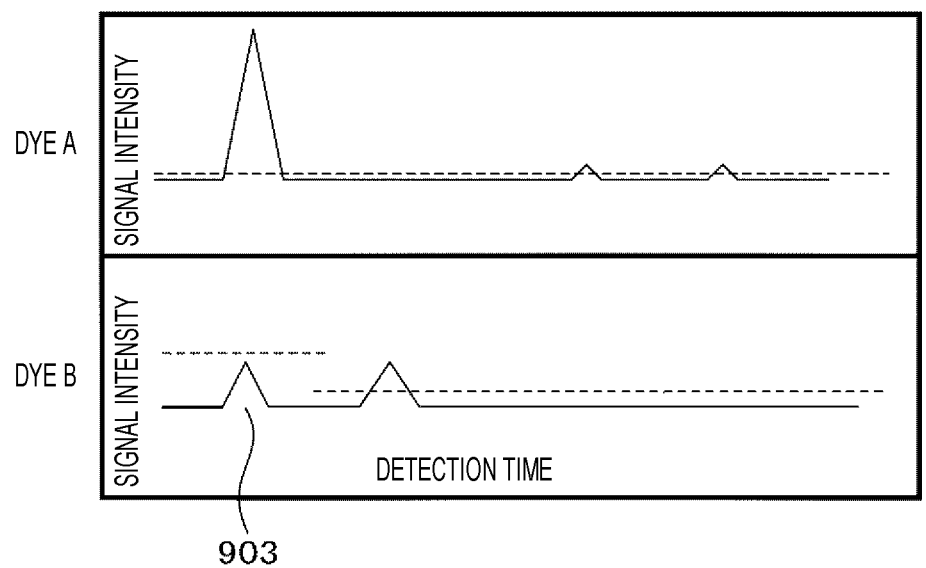
FIG. 9D is a diagram illustrating an exemplary signal waveform showing effects of the present embodiment.

As a result, a level of influence by the pull-up peak can be known. If the lower threshold is not changed, the peak is determined as being above the threshold as denoted with 902 in FIG. 9C. Recalculating the threshold and changing the lower threshold as illustrated in FIG. 9D allows for determining the peak as being a false peak influenced by the pull-up peak as denoted with 903.

Furthermore, in a case where detection is performed in short and long exposure times as illustrated in FIG. 9, for example, even when a peak is recognizable in the long exposure time while the peak is not recognizable in the short exposure time, by combining data in the short and long exposure times, data of peaks recognizable using optimum thresholds according to the aforementioned procedure may be used as single data. For example, if a peak is below the lower threshold in the short exposure time but above the lower threshold in the long exposure time, peak data in the long exposure time is employed.

(10) Step 609: Also, when normalization has been performed for equalizing signal intensity at a constant value from a viewpoint that fluorescence intensity, obtained from the labeled DNA fragment of the known size used in step 607, is equal among the respective capillaries, a coefficient used for the normalization is also applied to a threshold and recalculation and resetting are performed along with the normalization.

(11) Step 610: With the recalculated threshold, association is established with the advance information of the target allele (allele calling).

(12) Step 611: Calculate a base length or the number of repetitions of a sequence and obtain profile data. This profile data obtained does not require interpretation by an expert or the like.

Figure 6:
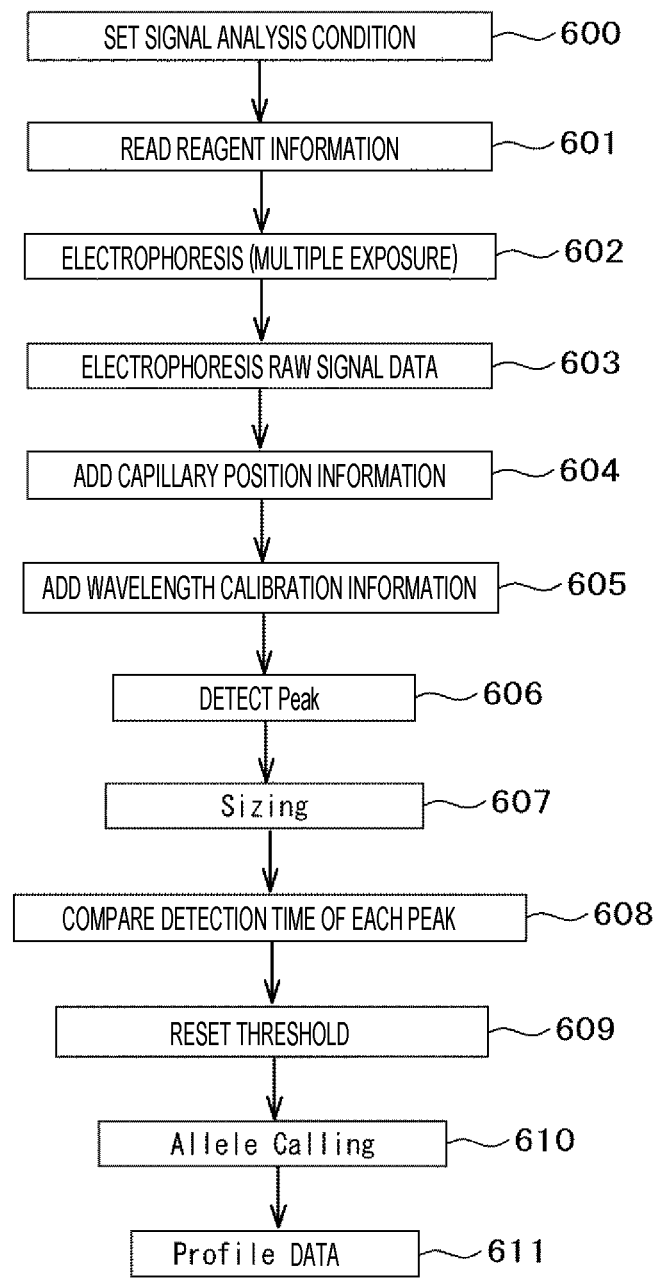
FIG. 6 is a flow chart illustrating an STR analysis procedure according to the present embodiment.

The flowchart illustrated in FIG. 6 is an example and thus the order of analysis may be changed. For example, step 608 where the pull-up peak is determined may be performed after step 603 where signals are acquired and step 606 where peaks are detected. Generally, electrophoresis is performed by an electrophoresis device and data therefrom is analyzed by a separate analysis software. By performing the analysis in the aforementioned procedure, the pull-up peak may be displayed on the electrophoresis device. Alternatively, influence by the pull-up may be considered in advance and subtracted from a fluorescence signal peak of other dye influenced before displaying the peak.

Figure 10:
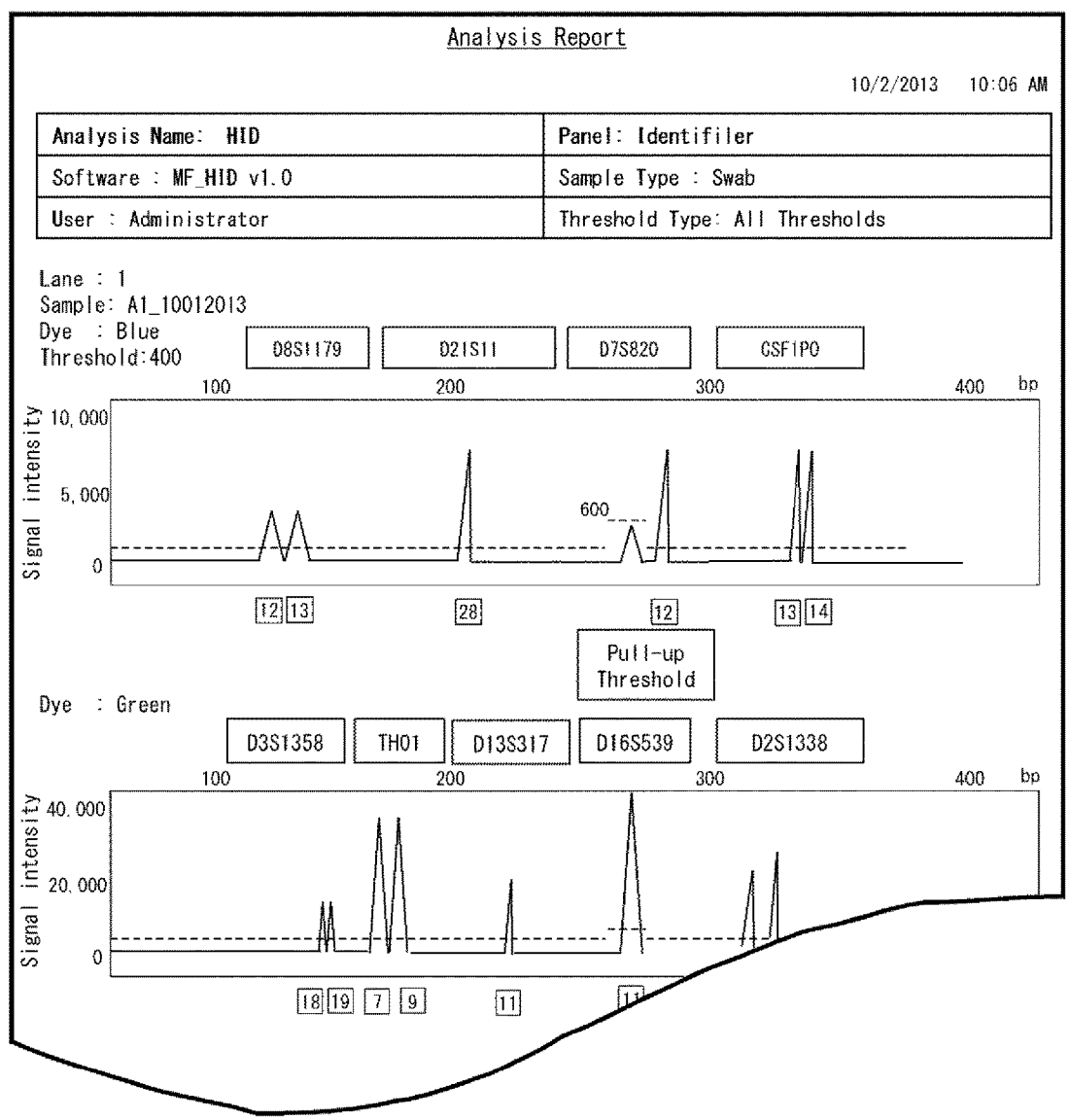
FIG. 10 is a diagram illustrating an exemplary output screen of a report according to the present embodiment.

A report of data acquired can be displayed on the control computer or printed. FIG. 10 illustrates an exemplary report. The report includes software used for the analysis and a version thereof, reagent type, sample type, and conditions for thresholds. Whether to apply each of the thresholds is selectable with a checkbox or the like on the setting screen illustrated in FIG. 7. Selected threshold items or values may be included in the report. The report may include actual waveform data and information on each allele (e.g. the number of repetitions). A peak where the threshold is reset according to the present invention may be illustrated as follows. As illustrated in a waveform with a dye in blue in FIG. 10, a threshold may be illustrated by a dotted line with a reset part denoted with "Pull-up Threshold."

In FIG. 10, a contributing factor to modification of the threshold, which is the pull-up, is displayed; however, all the thresholds having been applied may be displayed. Modification of a threshold such as an operation of adding or removing a threshold may be performed on the screen of the control computer.

As described above, the present invention allows for estimating a pull-up peak from signals obtained in the same detection time as that of signal characteristic having been evaluated in advance. Furthermore, according to the present invention, determination based on knowledge and experience of an expert is not required, thereby allowing for automatic discrimination of a false peak and simplifying the analysis.

Furthermore, combining a plurality of excitation light irradiation times and estimating the pull-up peak from signals obtained in the same detection time as that of signal characteristic having been evaluated in advance allows for determination on whether the obtained peak is a false peak influenced by the pull-up attributable to saturation in other wavelength.

Moreover, by calculating the pull-up peak by identifying the parent peak, estimating, as a fixed value, a maximum value of false signals including those of the pull-up peak and setting an excessive threshold are not required. As a result, a true peak, which has been excluded due to estimation of the maximum value, is not excluded. In other words, expanding a lower detection range allows for, for example, an adjustment function of sample concentration to be no longer required, thereby allowing for the speedy and downsized device.

REFERENCE SIGNS LIST

101: device main body
102: capillary
103: pump mechanism
104: high voltage power supply
105: syringe
106: gel block
107: polymer container
108: anode buffer container
109: anode electrode
110: electric valve
111: light source
112: optical detector
113: detecting unit
114: multi-capillary array
115: thermostatic chamber
116: fan
117: heating and cooling mechanism
118: buffer container
119: washing container
120: waste liquid container
121: sample container
122: conveyor
123: moving stage
124: load header
125: control computer
126: capillary cathode edge
127: control substrate
128: detected data
201: laser beam
202: reflection mirror
203: beam splitter
204: condenser lens

The invention claimed is:
1. A nucleic acid analysis method comprising:
irradiating, with light, an analysis sample including a plurality of DNA fragments;
detecting fluorescence, excited from the analysis sample, corresponding to the DNA fragments with an imaging element within a predetermined detection time;
setting a lower limit of fluorescence intensity required for analysis of the analysis sample within a detectable range of fluorescence intensity of the imaging element;
acquiring fluorescence intensity for each of the DNA fragments at a plurality of wavelengths based on the lower limit;
detecting two or more peaks of the fluorescence intensity acquired for each of the DNA fragments and determining time information corresponding to the two or more peaks;
comparing detection times of the two or more peaks for each of the DNA fragments to determine a first peak of the two or more peaks at a first wavelength having a first fluorescence intensity and a second peak of the two or more peaks at a second wavelength having a second fluorescence intensity weaker than the first fluorescence intensity, the first peak and the second peak having a same detection time, and determining the second peak as a false signal peak;
adjusting the lower limit of fluorescence intensity for the second peak based on the fluorescence intensity of the first peak and a predetermined value; and
displaying correspondence of the fluorescence intensity to the time information for each of the DNA fragments,
wherein the displayed correspondence of the fluorescence intensity to the time information for each of the DNA fragments includes displaying the first peak having the first fluorescence intensity at the first wavelength and the second peak for the second wavelength, and
wherein the first peak is displayed with the set lower limit of fluorescence intensity and the second peak is displayed with the adjusted lower limit of fluorescence intensity.

2. The nucleic acid analysis method according to claim 1, wherein the predetermined value is a fixed value preset based on performance of a device used in analysis of the analysis sample and use condition of the device.

3. The nucleic acid analysis method according to claim 1, wherein the predetermined value is preset and calculated with a ratio using the first peak as a reference.

4. The nucleic acid analysis method according to claim 3, wherein an adjusted peak value is obtained by subtracting the predetermined value, calculated with the ratio using the first peak as a reference, from the second peak.

5. The nucleic acid analysis method according to claim 1, wherein the predetermined value varies according to an analysis method of the analysis sample.

6. The nucleic acid analysis method according to claim 1, wherein the irradiating of the analysis sample includes at least two irradiation times different from each other.

7. The nucleic acid analysis method according to claim 1, wherein information including the adjusted lower limit is displayed in a form of a report.

8. The nucleic acid analysis method according to claim 1, wherein the first wavelength corresponds to a first dye in the analysis sample, and the second wavelength corresponds to a second dye in the analysis sample.

9. A nucleic acid analyzer comprising:
a light irradiating unit configured to irradiate, with light, an analysis sample including a plurality of DNA fragments;
a detecting unit configured to detect fluorescence intensity, excited from the analysis sample, corresponding to the DNA fragments with an imaging element within a predetermined detection time;
a storage configured to store a lower limit of fluorescence intensity required for analysis of the analysis sample within a detectable range of fluorescence intensity of the imaging element;
an arithmetic control unit configured to control the respective units and to perform arithmetic processing; and
a display unit configured to display a result from the arithmetic control unit,
wherein the detecting unit is further configured to acquire fluorescence intensity for each of the DNA fragments at a plurality of wavelengths based on the lower limit,
the arithmetic control unit is further configured to:
detect two or more peaks of the fluorescence intensity acquired for each of the DNA fragments and determine time information corresponding to the two or more peaks,
compare detection times of the two or more peaks for each of the DNA fragments to determine a first peak of the two or more peaks at a first wavelength having a first fluorescence intensity and a second peak of the two or more peaks at a second wavelength having a second fluorescence intensity weaker than the first fluorescence intensity, the first peak and the second peak having a same detection time, and determine the second peak as a false signal peak,
adjust the lower limit of fluorescence intensity for the second peak based on the fluorescence intensity of the first peak and a predetermined value, and
display correspondence of the fluorescence intensity to the time information for each of the DNA fragments on the display unit,
wherein the display of the correspondence of the fluorescence intensity to the time information for each of the DNA fragments includes displaying the first peak having the first fluorescence intensity and the second peak for the second wavelength, and
wherein the arithmetic control unit is further configured to display the first peak with the set lower limit of fluorescence intensity and the second peak with the adjusted lower limit of fluorescence intensity.

10. The nucleic acid analyzer according to claim 9, wherein the predetermined value is a fixed value preset based on performance of a device used in analysis of the analysis sample and use condition of the device.

11. The nucleic acid analyzer according to claim 9, wherein the predetermined value is preset and calculated with a ratio using the first peak as a reference.

12. The nucleic acid analyzer according to claim 11, wherein an adjusted peak value is obtained by subtracting the predetermined value, calculated with the ratio using the first peak as a reference, from the at least one or more of the peaks including the second peak.

13. The nucleic acid analyzer according to claim 9, wherein the predetermined value varies according to an analysis method of the analysis sample.

14. The nucleic acid analyzer according to claim 9, wherein the predetermined detection time includes at least two irradiation times different from each other.

15. The nucleic acid analyzer according to claim 9, wherein information including the adjusted lower limit is displayed on the display unit in a form of a report.

16. The nucleic acid analyzer according to claim 9, wherein the first wavelength corresponds to a first dye in the analysis sample, and the second wavelength corresponds to a second dye in the analysis sample.

* * * * *